United States Patent [19]

Green

[11] 4,401,649
[45] Aug. 30, 1983

[54] SUNSCREEN METHOD

[75] Inventor: Milton Green, Newtown Center, Mass.

[73] Assignee: Polaroid Corporation, Cambridge, Mass.

[21] Appl. No.: 284,624

[22] Filed: Jul. 20, 1981

[51] Int. Cl.³ ............................................... A61K 7/44
[52] U.S. Cl. .......................................... 424/60; 424/59
[58] Field of Search ............................................ 424/60

[56] References Cited

U.S. PATENT DOCUMENTS

| | | | |
|---|---|---|---|
| 2,395,665 | 2/1946 | Isermann et al. | 424/60 |
| 3,271,440 | 9/1966 | Thomas | 260/471 |
| 3,403,207 | 9/1968 | Kreps et al. | 424/60 |
| 3,719,692 | 3/1973 | Havinga et al. | 260/404.5 |
| 3,751,563 | 8/1973 | Richardson | 424/60 |
| 3,891,693 | 6/1975 | Preston | 260/471 R |
| 3,932,360 | 1/1976 | Cerankowski et al. | 260/77.5 AM |
| 4,069,309 | 1/1978 | Ciaudelli et al. | 424/47 |
| 4,078,054 | 3/1978 | Isermann et al. | 424/60 |
| 4,115,547 | 9/1978 | Degen | 424/60 |
| 4,132,774 | 1/1979 | Strobel | 424/60 |
| 4,150,114 | 4/1979 | Smith | 424/60 |

Primary Examiner—Dale R. Ore
Attorney, Agent, or Firm—Louis G. Xiarhos

[57] ABSTRACT

Sunscreen compositions are described which comprise a pharmaceutically acceptable carrier having incorporated therein, in an amount effective to provide protection against the harmful effects of ultraviolet radiation, a compound of the formula

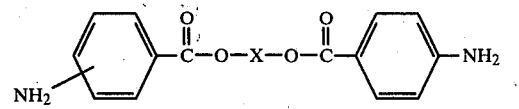

wherein X is an alkylene group containing 1 to 7 carbon atoms and the amino group of unspecified position is substituted meta or para to the ester group.

8 Claims, No Drawings

SUNSCREEN METHOD

BACKGROUND OF THE INVENTION

The present invention relates to sunscreen compositions. More particularly, the present invention relates to sunscreen compositions comprising, as a sunscreening agent, a bis(aminobenzoate)ester of certain alkylene diols or polyols, and to a method for protecting against the harmful effects of ultraviolet radiation employing the sunscreen compositions.

It is well known that sunburn is principally due to exposure of the skin to ultraviolet radiation in the 290 nanometer (nm.) to 320 nm. range. Radiation in this region can result in severe erythema, edema, blistering, and other severe damage to the skin. In contrast, at wavelengths greater than about 320 nm. damage to the skin is relatively slight and the wavelengths in the 320 nm. to 400 nm. range are generally regarded as promoting only tanning of the skin (the so-called tanning region).

Various agents have been proposed for use in cosmetic sunscreen preparations intended to protect against the harmful effects of ultraviolet radiation while permitting desired tanning of the skin. Ideally, the sunscreen agent, when topically applied, is capable of absorbing at least a major portion of the incident radiation in the 290–320 nm. range so as to protect against the harmful effects thereof, and is transparent to wavelengths greater than about 320 nm., thereby permitting the desired tanning effects of the longer wavelength radiation. The sunscreen agent is normally incorporated in a dermatologically innocuous carrier so as to provide a cosmetically acceptable and appealing preparation. In general, the carrier permits convenient topical application of the preparation. Included among the compounds proposed for use as sunscreen agents are p-aminobenzoic acid and certain of its esters, N,N-dimethyl-p-aminobenzoic acid esters, p-methoxy cinnamic acid esters, variously substituted benzophenones, e.g., 2-hydroxy-4-methoxybenzophenone and 2,4-dihydroxybenzophenone, and various salicylates such as phenyl salicylate and 2-ethylhexylsalicylate.

SUMMARY OF THE PRESENT INVENTION

The present invention relates to new sunscreen compositions and to a method for protecting against the harmful effects of ultraviolet radiation employing the instant compositions. In particular, the present invention relates to sunscreen compositions comprising a pharmaceutically acceptable carrier having incorporated therein, in an amount effective to provide protection against the harmful effects of ultraviolet radiation, a compound of the formula

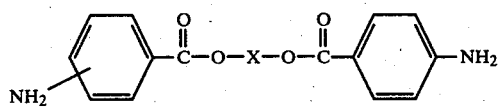

wherein X is an alkylene group containing 1 to 7 carbon atoms and the amino group of unspecified position is substituted meta or para to the ester group. In a highly preferred embodiment, the compound is present in the composition as a solute, i.e., the carrier is comprised of a suitable solvent for the compound.

The method of this invention comprises topically applying a sunscreen composition of this invention to the skin in an amount sufficient to provide protection against the harmful effects of ultraviolet radiation.

For a fuller description and understanding of the present invention, reference should be had to the following detailed description.

DETAILED DESCRIPTION OF THE INVENTION

The present invention provides novel sunscreen compositions comprising, as a sunscreening agent, a bis-(aminobenzoate) ester of certain alkylene diols and polyols comprising from 1 to 7 carbon atoms. Specifically, the present invention provides sunscreen compositions comprising a pharmaceutically acceptable carrier having incorporated therein, in an amount effective to provide protection against the harmful effects of ultraviolet radiation, a compound of the formula

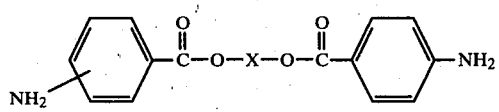

wherein X is an alkylene group containing 1 to 7 carbon atoms and the amino group of unspecified position is substituted meta or para to the ester group. Compounds of the above formula are employed in the compositions of this invention as sun-screening agents and are particularly appropriate for such use in that they are capable of absorbing a very high percentage of incident radiation in the 290 nm. to 320 nm. range and yet are effectively transparent to wavelengths above about 320 nm.

The alkylene group X of the sunscreening compounds can be a straight, branched, or cyclic alkylene group containing from 1 to 7 carbon atoms. The alkylene group may be substituted with substituents such as oxo, chloro, bromo, or hydroxy, and such substituents may be present for purposes of providing desired physical or chemical characteristics to the sunscreen compound, e.g., a desired degree of substantivity or solubility. In a preferred embodiment, the alkylene group contains an odd number of carbon atoms, most preferably 3 to 5 carbon atoms. Particularly preferred sunscreen compounds of this invention are those wherein X contains 3 or 5 carbon atoms and both amino groups are substituted in the para position with respect to the ester groups, such an amino group substitution pattern having been found to provide maximum ultraviolet absorbing capability in the 290–320 nm. region.

The subject sunscreen agents are known materials and do not, per se, constitute a part of this invention. They may be considered to be bis(aminobenzoate)esters of appropriate alkylene diols or polyols and, in general, may be prepared by reaction of para-nitrobenzoyl chloride or a mixture of para- and meta-nitrobenzoyl chloride with an alkylene diol or the primary hydroxy groups of an alkylene polyol and reduction of the thus-formed compound to a diamine. Disclosure pertaining to such a preparative method is contained in U.S. Pat. No. 3,271,440, issued Sept. 6, 1966, and in U.S. Pat. No. 3,932,360, issued Jan. 13, 1976. Alkylene diols useful in preparing the sunscreen agents of this invention include:
ethylene glycol
1,3-propane diol
1,3-butane diol
1,4-butane diol 2,3-butane diol
3-chloro-1,2-propane diol
2,2-dimethyl-1,3-propane diol
1,2-propane diol
1,5-pentanediol
1,6-hexane diol
1,4-cyclohexane diol Alkylene polyols useful in preparing the sunscreen agents of this invention include glycerol, erythritol, arabitol, and mannitol. Included among the sunscreen agents which may be employed in the compositions of this invention are the following:

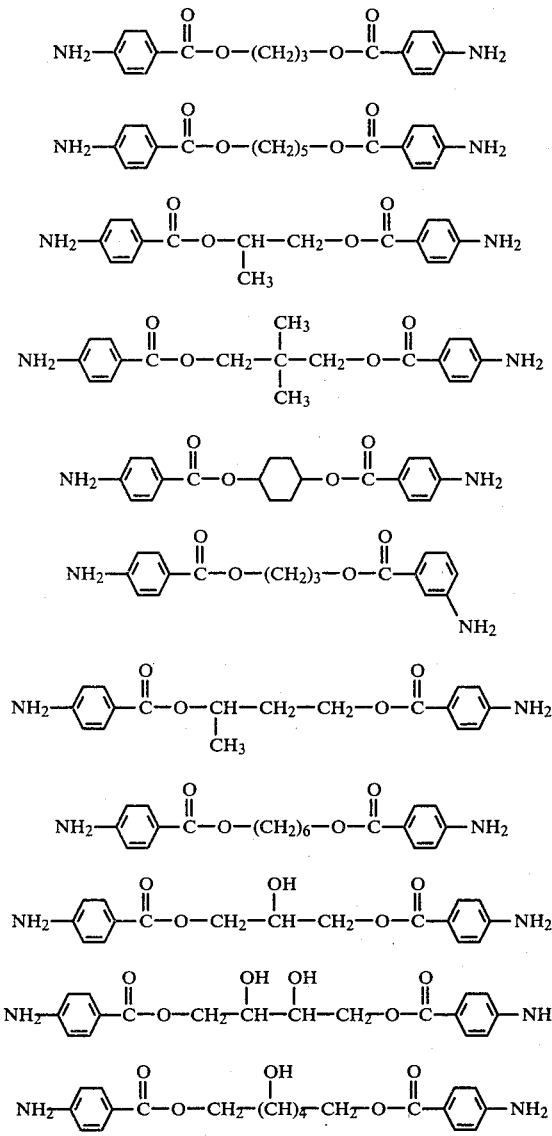

As indicated above, the compositions of the invention comprise the sunscreen compound in an amount effective to provide protection against the harmful effects of ultraviolet radiation. Thus, the amount or concentration of sunscreen compound in the composition is such that, when the composition is topically applied, the desired protection is provided. The amount needed to provide the desired protection can vary with the characteristics of the sunscreen compound, e.g., its extinction coefficient or substantivity, the nature of the carrier, the source and intensity of the radiation, and other well-recognized variables. Suitable amounts can be readily determined by standard methods of dermatological testing. Preferably, the sunscreen compound is incorporated in the composition in an amount of about 5% to about 50% by weight and more preferably about 10% to about 30% by weight.

The pharmaceutically acceptable carrier of the present compositions can be any vehicle or medium capable of incorporating the sunscreen agent in a manner permitting uniform topical application. The term "pharmaceutically acceptable" is intended as a term of qualification in that the carrier should be dermatologically innocuous and cosmetically acceptable. The carrier may comprise an oil or cream base material in which the agent can be held in a uniform dispersion, e.g., as submicron sized particles. Preferably, the carrier comprises a suitable solvent or mixture of solvents capable of dissolving the sunscreen agent in an effective concentration, i.e., the effective amount of sunscreen agent is incorporated in the sunscreen composition as a solute. Solvents which may be employed include dimethylsulfoxide and polyether polyols having a molecular weight of about 400 to about 4000. The polyether polyols are a well known class of chemical compounds and have been disclosed for use in a number of applications, most notably in the preparation of polyurethane foams. Preferred polyether polyols are those having a primary hydroxyl content of about 70% or greater. Commercially available polyols of the preferred type include those available from the Olin Corp., Stamford, CT., under the tradenames Poly G55-173/diol, Poly G55-112/diol, and Poly G76-120/triol. Information pertaining to the solubility of one of the sunscreen compounds hereof, viz., the bis(p-aminobenzoate)ester of 1,3-propane diol, in the named commercially available polyols is available in the commercial bulletin published by the Polaroid Corp., Cambridge, MA., entitled Polagram, vol. 2, ed. 1, March 1981. As described therein, various concentrations of the bis(p-aminobenzoate)ester of 1,3-propane diol were solubilized in the named polyols and the solutions evaluated at 120° F., 75° F., and 60° F. for six weeks. The reported results of this evaluation are reproduced below and indicate the upper weight concentrations of the ester that can be dissolved in the respective polyols to produce stable solutions:

| polyol | approx. MW | 120° F. | 72° F. | 60° F. |
| --- | --- | --- | --- | --- |
| PolyG55-173/diol | 650 | <30% >25% | <30% >25% | <30% >25% |
| PolyG55-112/diol | 1000 | <25% >20% | <25% >20% | <25% >20% |
| PolyG76-120/triol | 1500 | 20% | 20% | 20% |

In the sunscreen compositions of this invention, the polyol solvents may be employed alone or admixed with one or more miscible liquids or solvents, e.g., one of the various alcohols such as ethanol or isopropanol.

As is common in the art, it is preferred that the sunscreen agents employed in the compositions of this invention have a high degree of purity. The utilization of highly pure sunscreen agents is particularly preferred insofar as it insures against the presence of impurities which may induce an adverse dermatological reaction or adversely impact the ultraviolet protective function of the sunscreen composition, e.g., photosensitizing agents. Purification of the sunscreen agents of this invention may be accomplished by various techniques known in the chemical art, e.g., chromatographic or recrystallization techniques.

The sunscreen compositions of this invention may contain additives other than those specifically mentioned herein, such as surfactants, emollients, perfumes, antioxidants, artificial tanning agents such as dihydroxyacetone, and conventional sunscreening agents such as p-aminobenzoic acid. Two or more of the sunscreening agents of this invention may be employed in combination in the instant compositions.

The following non-limiting example illustrates a composition of the present invention.

EXAMPLE

The bis(p-aminobenzoate)ester of 1,3-propanediol (commercially available from the Polaroid Corp., Cambridge, MA., under the tradename Polacure 740 M) was dissolved in dimethylsulfoxide in a concentration of 25% by weight. The solution was topically applied to various sites on two albino guinea pigs. The sites were exposed to ultraviolet radiation in the 290-320 nm. range, different sites receiving different doses of up to 14 MED (minimal erythemal doses). Excellent protection against the erythemal effects of the radiation was observed at all dosages.

Regarding the method aspect of this invention, there is provided a method for protecting against the harmful effects of ultraviolet radiation which comprises topically applying a sunscreen composition of this invention to the skin in an amount sufficient to provide the desired protection.

What is claimed is:

1. A method for protecting against the harmful effects of ultraviolet radiation in the range of 290 nanometers to 320 nanometers comprising topically applying a sunscreen composition comprising a pharmaceutically acceptable carrier having incorporated therein, in an amount effective to provide protection against the harmful effects of ultraviolet radiation, a compound of the formula

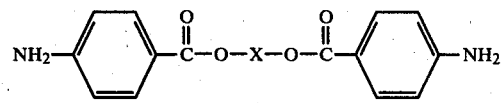

wherein X is an alkylene group containing 3 or 5 carbon atoms, said sunscreen composition being applied to the skin in an amount sufficient to provide said protection.

2. A method of claim 1 wherein said compound is incorporated in said composition in an amount of about 5% to about 50% by weight.

3. A method of claim 2 wherein said compound is incorporated in said composition in an amount of about 10% to about 30% by weight.

4. A method of claim 1 wherein said compound is dissolved in said carrier.

5. A method of claim 4 wherein said carrier comprises, as a solvent for said compound, dimethylsulfoxide.

6. A method of claim 4 wherein said carrier comprises, as a solvent for said compound, a polyether polyol having a molecular weight of about 400 to about 4000.

7. A method of claim 6 wherein said polyether polyol has a primary hydroxyl content of about 70% or greater.

8. A method of claim 1 wherein said compound is of the formula

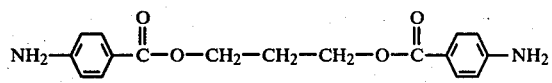

* * * * *